United States Patent [19]

Prospero et al.

[11] Patent Number: 5,666,782
[45] Date of Patent: Sep. 16, 1997

[54] FIXTURE FOR ASSEMBLING DENTAL FLOSS DISPENSER PRODUCTS

[75] Inventors: Richard M. Prospero, Princeton; Erik Lunde, Morganville; Harry Swanson, Bloomfield; Lee Adams, Flemington, all of N.J.

[73] Assignee: Johnson & Johnson Consumer Products, Inc., Skillman, N.J.

[21] Appl. No.: 381,512

[22] Filed: Jan. 31, 1995

[51] Int. Cl.⁶ .................................................. B65B 35/54
[52] U.S. Cl. .......................... 53/155; 53/118; 53/169; 53/173; 53/238; 29/430; 29/469; 29/784; 29/799
[58] Field of Search .................. 53/116, 118, 155, 53/157, 168, 169, 170, 173, 237, 238, 240; 29/33 K, 429, 430, 469, 773, 784, 799, 564.1

[56] References Cited

U.S. PATENT DOCUMENTS

| | | |
|---|---|---|
| 2,929,541 | 3/1960 | Castelli et al. . |
| 3,246,815 | 4/1966 | Aronson . |
| 3,325,889 | 6/1967 | Meli et al. ............................ 53/118 X |
| 3,480,190 | 11/1969 | Freedman . |
| 3,930,059 | 12/1975 | Wells . |
| 4,034,770 | 7/1977 | Trecker . |
| 4,162,688 | 7/1979 | Tarrson et al. . |
| 4,365,458 | 12/1982 | Palmer et al. ............................ 53/173 X |
| 4,531,284 | 7/1985 | Matsuura et al. ............................ 29/784 |
| 4,662,166 | 5/1987 | Oexler et al. . |
| 4,706,843 | 11/1987 | Thornton . |
| 4,815,190 | 3/1989 | Haba, Jr. et al. ............................ 29/430 |
| 4,884,330 | 12/1989 | Sticht ............................ 29/784 X |
| 4,925,073 | 5/1990 | Tarrson et al. . |
| 5,156,311 | 10/1992 | Spencer, Jr. et al. . |
| 5,305,768 | 4/1994 | Gross et al. . |

*Primary Examiner*—Daniel Moon

[57] ABSTRACT

A method and apparatus for assembling a dental floss product formed of a bobbin of wound thread, a dispenser case, and a dispenser insert for rotatably supporting the bobbin of wound thread when positioned within the dispenser case. The dispenser insert is detachably mounted in an insert loading area of a singular dispenser assembly fixture, and the dispenser case is detachably mounted in a dispenser case loading area of the singular dispenser assembly fixture. The bobbin of wound thread is next loaded onto the dispenser insert while the dispenser insert is mounted in the insert loading area. The dispenser insert with the bobbin of wound thread loaded thereon is then detached from the insert loading area, and the dispenser insert with the bobbin of wound thread loaded thereon is loaded into the dispenser case while the dispenser case is mounted in the dispenser case loading area. The lid of the loaded dispenser case is then closed, and the dispenser case is detached from the dispenser case loading area.

7 Claims, 6 Drawing Sheets

5,666,782

FIXTURE FOR ASSEMBLING DENTAL FLOSS DISPENSER PRODUCTS

FIELD OF THE INVENTION

The present invention relates generally to systems for manufacturing and assembling devices for distributing threads. More particularly, the present invention relates to systems for assembling devices for dispensing individual bobbins of wound thread. Still more particularly, the present invention relates to automated systems for assembling dental floss products.

BACKGROUND OF THE INVENTION

Tooth decay and dental disease can be caused by bacterial action resulting from the formation of plaque about the teeth and/or the entrapment of food particles between the teeth and interstices therebetween. The removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. The term "dental floss", as used herein, is defined to include both dental flosses, dental tapes, threads and any similar article.

Dental floss is typically distributed in dispensers that have circular bobbins rotatably mounted therein. Each bobbin is formed of a core that has been wound with dental floss. The tail end of floss from the bobbin is typically threaded first through an eyelet at the top of the dispenser and then through a cut bar that is also positioned at the top of the dispenser. In order to draw a length of floss from the dispenser, a user grasps the tail end of the floss, pulls until the desired length of floss has been drawn from the dispenser, and then cuts the drawn length using the cut bar. As the user pulls the floss from the dispenser, the bobbin in the dispenser rotates, thereby allowing the floss on the bobbin to unwind.

During the manufacturing and assembly of dental floss products, automated winding machines are used to wind floss onto empty bobbin cores. These winding machines often function at a high speed and may wind many yards of dental floss each minute. After the dental floss is wound onto bobbin cores, the wound cores must then be loaded and threaded into dispenser inserts. Each dispenser insert typically includes a core holder for rotatably supporting the wound core when the wound core is positioned within a dispenser case. The eyelet and cut bar discussed above are typically part of and integral with the dispenser insert. After a wound core has been loaded on and threaded through the eyelet and cut bar in the dispenser insert, the dispenser insert is then placed within the dispenser case, and the lid to the dispenser case is closed.

At present, a significant percentage of dental floss products sold worldwide are assembled by hand. Although various systems have been proposed for assembling dental floss products in an automated fashion, these automated systems have suffered from several drawbacks. These drawbacks stemmed, at least in part, from the need to bring several components of the product (namely, the wound bobbin, the dispenser insert and the dispenser case) together simultaneously at the point of final assembly. In known systems, elaborate indexing systems were required to bring these components together in synchronization. Besides being complicated and expensive, these indexing systems had many moving parts and were therefore subject to breakdown.

It is therefore an object of the present invention to provide an efficient and cost-effective automated system for assembling dental floss products.

It is a further object of the present invention to provide an automated system for assembling dental floss products that does not require the use of multiple indexing systems.

These and still other objects of the invention will become apparent upon study of the accompanying drawings and description of the invention.

SUMMARY OF THE INVENTION

The present invention is directed to a method and apparatus for assembling a dental floss product formed of a bobbin of wound thread, a dispenser case, and a dispenser insert for rotatably supporting the bobbin of wound thread when positioned within the dispenser case. The dispenser insert is detachably mounted in an insert loading area of a singular dispenser assembly fixture, and the dispenser case is detachably mounted in a dispenser case loading area of the singular dispenser assembly fixture. The bobbin of wound thread is next loaded onto the dispenser insert while the dispenser insert is mounted in the insert loading area. The dispenser insert with the bobbin of wound thread loaded thereon is then detached from the insert loading area, and the dispenser insert with the bobbin of wound thread loaded thereon is loaded into the dispenser case while the dispenser case is mounted in the dispenser case loading area. The lid of the loaded dispenser case is then closed, and the dispenser case is detached from the dispenser case loading area.

DETAILED DESCRIPTION OF THE PREFERRED EMBODIMENT

Figure 1:
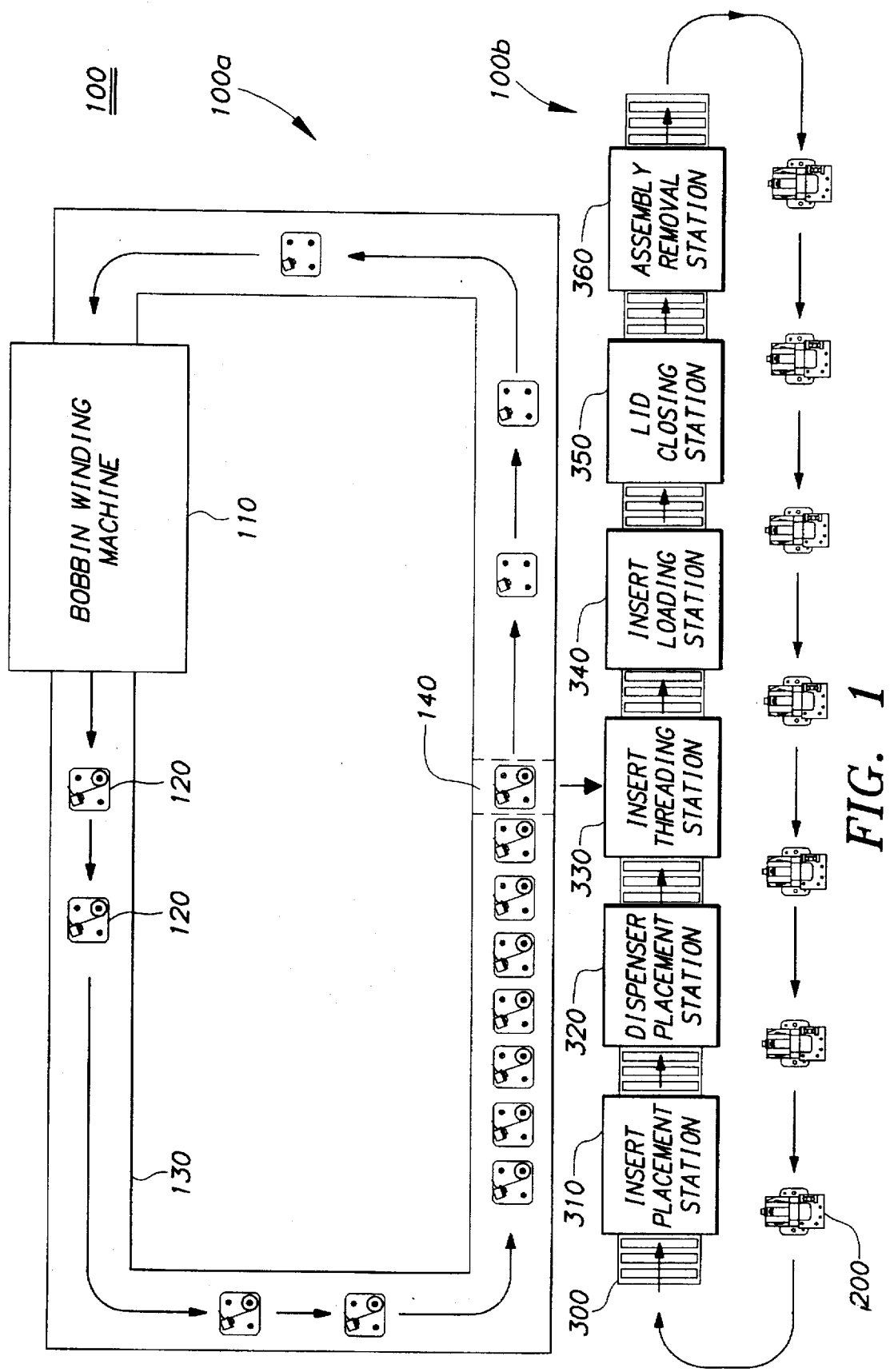
FIG. 1 is a block diagram of an automated system for manufacturing and assembling dental floss products in accordance with a preferred embodiment of the present invention.

Referring now to FIG. 1, there is shown a block diagram of an automated system 100 for manufacturing and assembly dental floss products in accordance with a preferred embodiment of the present invention. Automated system 100 is formed of a wound bobbin delivery loop 100a, and a dental floss product assembly loop 100b. In wound bobbin delivery loop 100a, dental floss is wound onto empty bobbin cores in bobbin winding machine 110. As wound bobbin cores are produced by bobbin winding machine 110, each wound bobbin core is placed on a pallet assembly 120. The wound bobbin cores are then carried on pallet assemblies 120 along track 130 in a circulating direction. As the pallet assemblies 120 reach bobbin removal station 140, the wound bobbins on pallet assemblies 120 are transferred into an insert threading station in dental floss product assembly loop 100b where the wound bobbins are used in assembling dental floss products. After the wound bobbins are removed from pallet assemblies 120 at removal station 140, the empty pallet assemblies 120 are recycled back to bobbin winding station 110 for further use. Further details of the operation of wound bobbin delivery loop 100a and pallet assemblies 120 are disclosed in U.S. patent application Ser. No. (unknown), entitled "Pallet Assembly for Detachably Mounting Bobbins," filed simultaneously herewith, the contents of which are hereby incorporated herein in their entirety by reference.

Dental floss product assembly loop 100b is formed of a conveyor assembly 300 with a plurality of assembly fixtures 200 rigidly affixed thereto. Conveyor assembly 300 repeatedly cycles each assembly fixture 200 through a series of six assembly stations each of which is used to perform a portion of the dental floss product assembly process. By way of an overview, conveyor assembly 300 begins by carrying an empty assembly fixture 200 to an insert placement station 310 where a dispenser insert is detachably mounted onto assembly fixture 200. Next, conveyor assembly 300 carries assembly fixture 200 to dispenser placement station 320 where an empty dispenser case is also detachably mounted onto assembly fixture 200. Following the placement of the dispenser insert and dispenser case onto assembly fixture 200, conveyor assembly 300 carries assembly fixture 200 to insert threading station 320 where a wound bobbin from wound bobbin delivery loop 100a is loaded on top of the dispenser insert on assembly fixture 200. In addition, the tail end of the wound bobbin delivered from loop 100a is threaded through the eyelet and cut bar of the dispenser insert at insert threading station 330. Next, the conveyor assembly 300 carries the assembly fixture 200 to an insert loading station 340, where the threaded dispenser insert is pushed (or loaded) into the empty dispenser case. After the dispenser insert has been loaded into the dispenser case, conveyor assembly 300 carries assembly fixture 200 to lid closing station 350, where the lid affixed to the dispenser case is closed. In the final step, assembly fixture 200 is carried to assembly removal station 360, where the assembled dental floss product is removed from assembly fixture 200. Following this operation at assembly removal station 360, the empty assembly fixture 200 is carried by conveyor assembly 300 back to insert placement station 310 for re-use.

Figure 2:
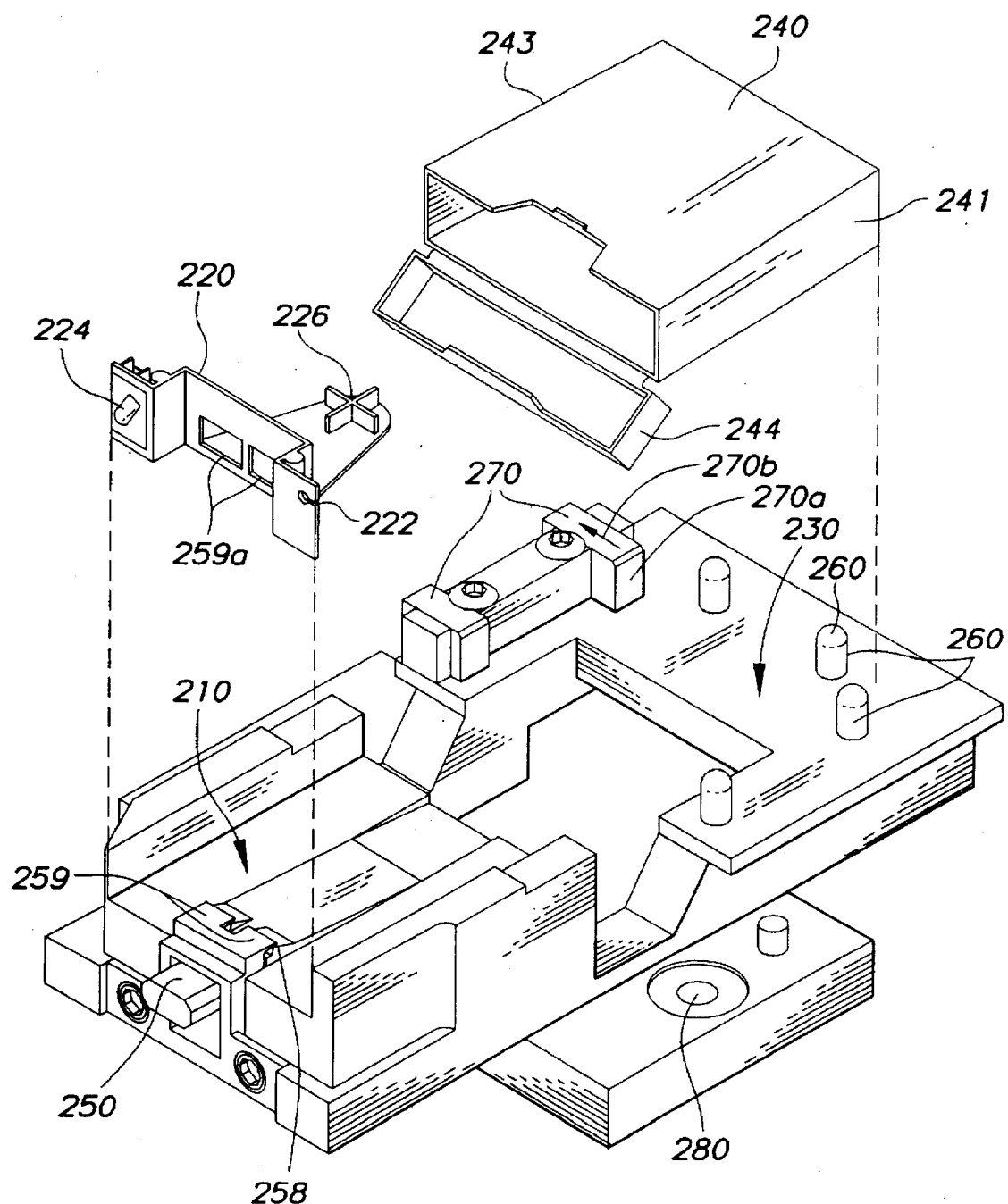
FIG. 2 is a perspective view of a fixture for assembling dental floss dispenser products in accordance with a preferred embodiment of the present invention.
Figure 3:
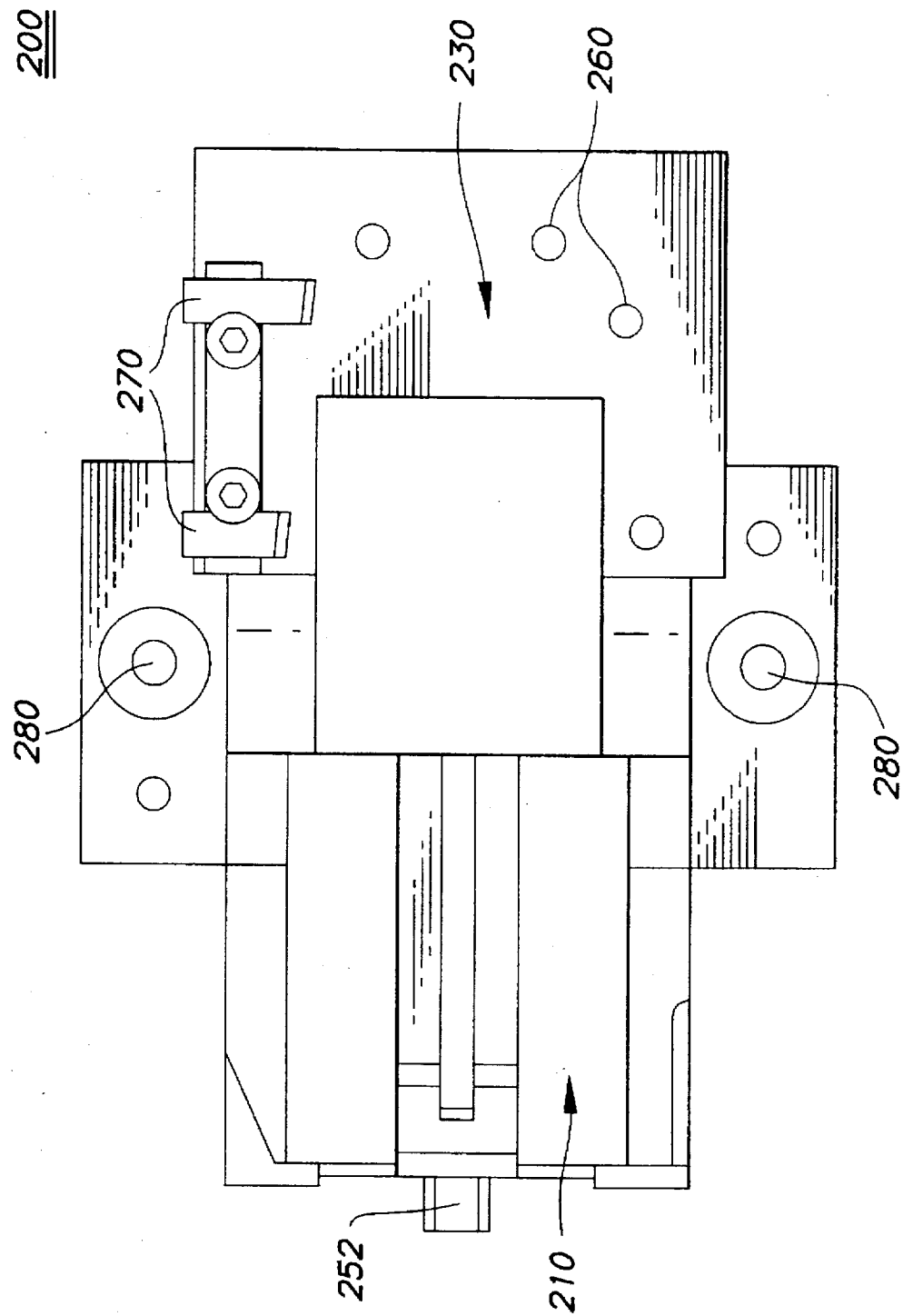
FIG. 3 is a top view of a fixture for assembling dental floss dispenser products in accordance with a preferred embodiment of the present invention.

Referring now to FIGS. 2 and 3, there are shown perspective and top views, respectively, of a fixture 200 for assembling dental floss products in accordance with a preferred embodiment of the present invention. Assembly fixture 200 includes an insert loading area 210 for receiving and holding a dispenser insert 220. Assembly fixture 200 also includes a dispenser case loading area 230 for receiving and holding a dispenser case 240. A depressable latch mechanism 250 is provided for detachably securing insert 220 in insert loading area 210. Among other functions, depressable latch mechanism 250 is used to detachably secure (or latch) insert 220 to assembly fixture 200 when assembly fixture 200 is in insert placement station 310. A plurality of mounting pins 260 and a pair of spring loaded cams 270 are provided for detachably securing dispenser case 240 in dispenser case loading area 230. Mounting pins 260 and spring loaded cams 270 are used to detachably secure dispenser case 240 to assembly fixture 200 when assembly fixture 200 is in dispenser placement station 320. In the preferred embodiment, assembly fixture 200 includes openings 280 for rigidly securing assembly fixture 200 to conveyor assembly 300 with bolts or other securing means.

Figure 4:
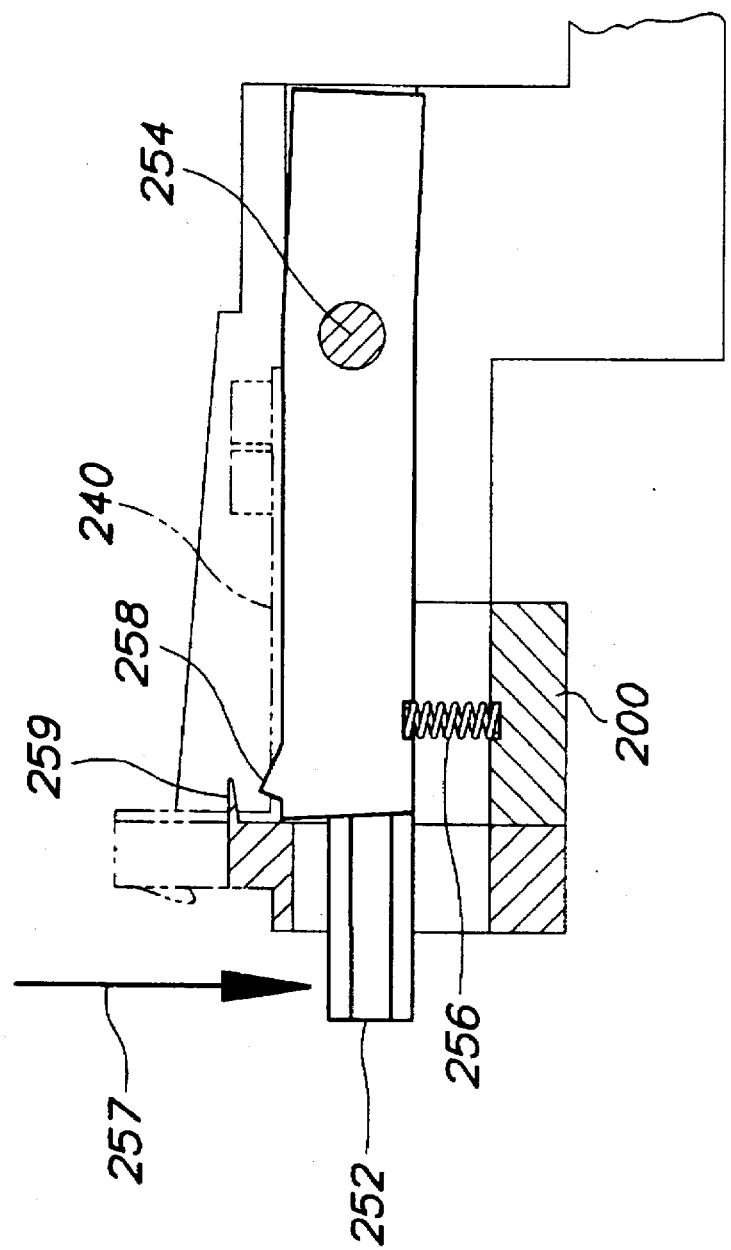
FIG. 4 is a partial cut-away view of a latching mechanism for detachably securing a dispenser insert to a fixture for assembling dental floss dispenser products in accordance with a preferred embodiment of the present invention.

Referring now to FIG. 4, there is shown a partial cut-away view of a latching mechanism 250 for detachably securing dispenser insert 220 to assembly fixture 200 in accordance with a preferred embodiment of the present invention. Latching mechanism 250 is formed of a latch release bar 252 which is pivotally coupled to assembly fixture 200 at pivot point 254. A depressable spring 256 is positioned between the latch release bar 252 and assembly fixture 200. Latch release bar 252 includes a securing ridge 258 for mating with a corresponding opening in insert 220. Securing ridge 258 functions to horizontally fix the position of insert 220 when insert 220 is latched in place. A pair of securing pins 259 are affixed to assembly fixture 200 and are provided for mating with corresponding openings 259a in insert 220. Securing pins 259 function to vertically fix the position of insert 220 when insert 220 is placed in insert loading area 210.

In the preferred embodiment, an insert 220 is detachably secured to assembly fixture 200 (in insert placement station 310) by first exerting a downward force against latch release bar 252 in the direction shown by arrow 257. After latch release bar 252 has been depressed downwardly, insert 220 is then placed into insert loading area 210 by aligning the securing pins 259 with the corresponding openings 259a in insert 220. After securing pins 259 and openings 259a are aligned, latch release bar 252 is then released, thereby allowing spring 256 to drive securing ridge 258 into its corresponding opening in insert 220.

As mentioned above, following the placement of insert 220 in insert loading area 210, conveyor assembly 300 carries assembly fixture 200 to a dispenser placement station 320 where a dispenser case 240 is detachably mounted in the dispenser case loading area 230 of assembly fixture 200. Dispenser case 240 is preferably mounted within loading area 230 by first aligning sides 241 and 242 of dispenser case 240 with mounting pins 260, and then exerting a downward force to "push" dispenser case 240 into loading area 230. This downward force causes springs (not shown) within spring loaded cams 270 to compress, thereby driving the mating faces 270a of spring loaded cams 270 backwards in the direction shown by arrow 270b. As mating faces 270a retract such that sufficient room is created for dispenser case 240 within loading area 230, dispenser case 240 falls downwardly bringing side 243 into contact with mating surfaces 270a. Once side 243 is brought into contact with mating surfaces 270a, an interference force created by spring loaded cams 270 maintains dispenser case 240 in a fixed position within dispenser case loading area 230.

Figure 5:
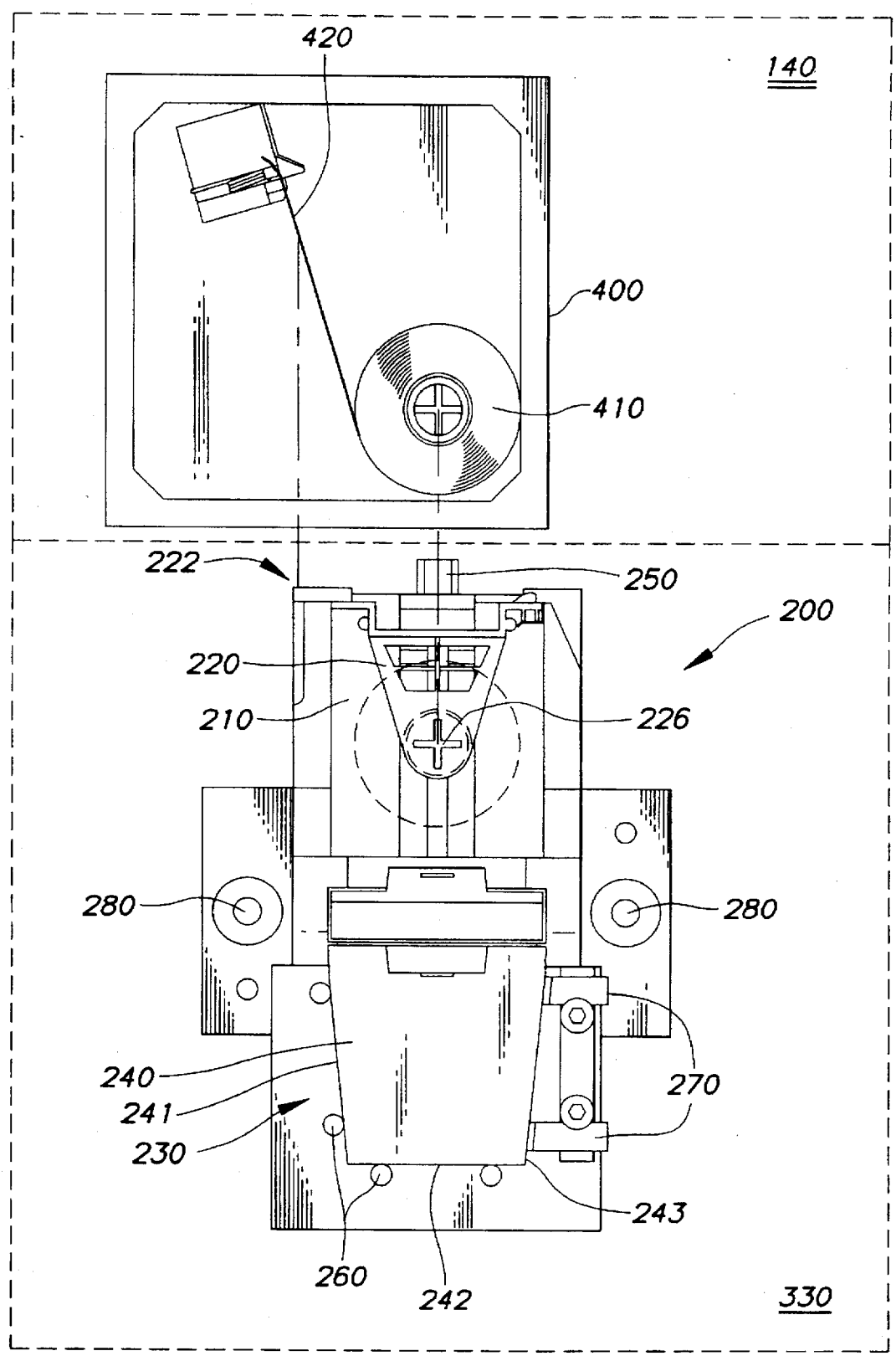
FIG. 5 is a top view showing a pallet assembly for holding a wound bobbin in alignment with a fixture for assembling dental floss dispenser products in accordance with a preferred embodiment of the present invention.

Following the mounting of dispenser case 240 onto assembly fixture 200, conveyor assembly 300 carries assembly fixture 200 to insert threading station 330 where a wound bobbin 410 from wound bobbin delivery loop 100a is loaded onto and threaded through insert 220. As explained more fully in co-pending U.S. patent application Ser. No. (unknown), entitled "Pallet Assembly for Detachably Mounting Bobbins," filed simultaneously herewith, each wound bobbin 410 is preferably delivered to threading station 330 by a pallet assembly 400. Referring now to FIG. 5, there is shown a top view illustrating the preferred placement and alignment of pallet assembly 400 and assembly fixture 200 employed for loading and threading wound bobbin 410 in threading station 330. In the preferred embodiment, prior to the loading of bobbin 410 onto insert 220, the center of bobbin 410 is aligned with the center of core holder 226 and, at the same time, the tail end 420 of the thread from bobbin 410 is aligned with eyelet 222. This alignment is preferred, because it allows mechanical systems (not shown) to place bobbin 410 on core holder 226 and thread tail end 420 through eyelet 222 without performing any angular rotations. A preferred system for used for grasping tail end 420 during threading operations is disclosed in co-pending U.S. application Ser. No. (unknown), entitled "Sinusoidal Anvil for Gripping Waxed Threads", filed simultaneously herewith, the contents of which are hereby incorporated herein in their entirety by reference.

Figure 6:
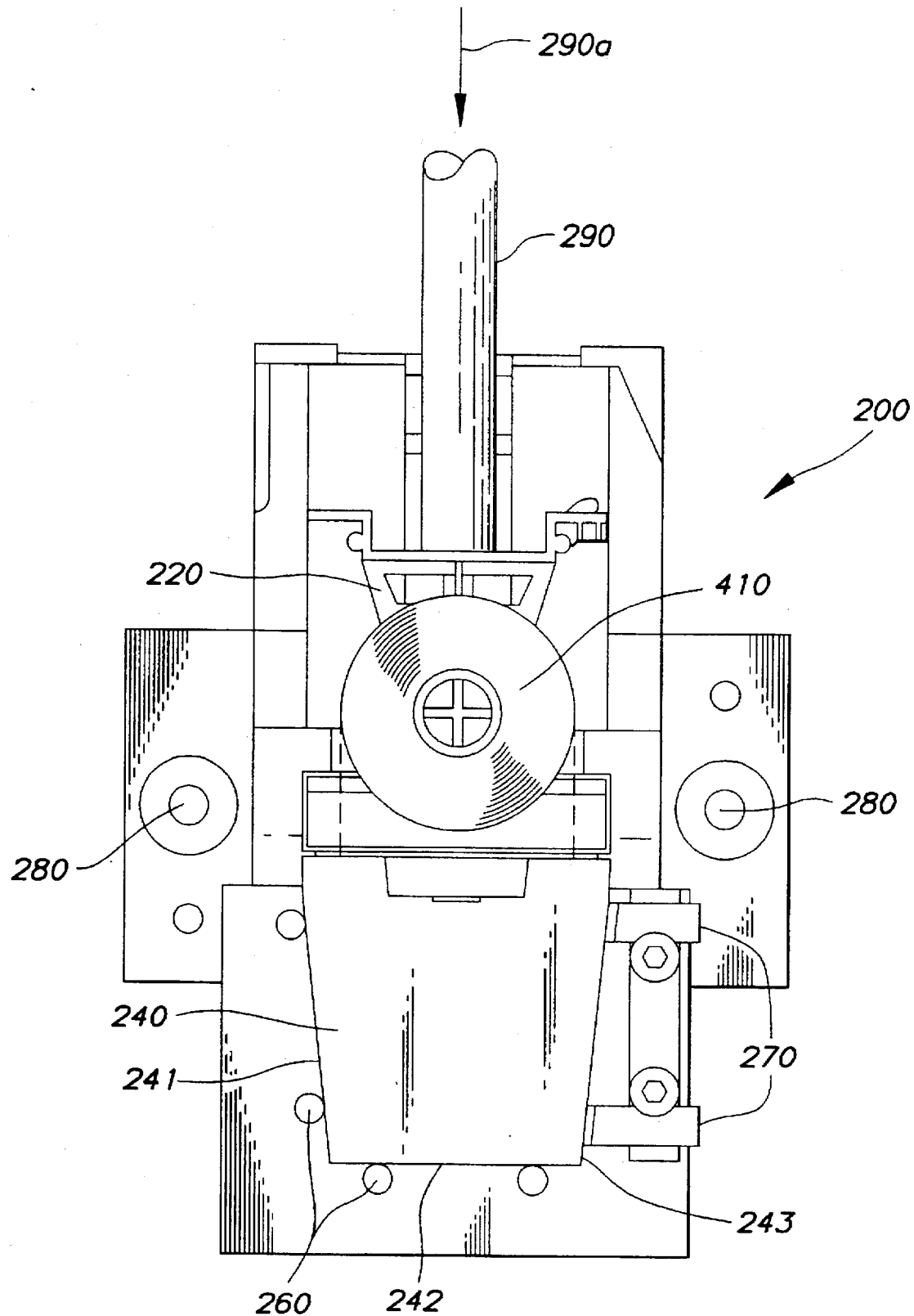
FIG. 6 is a further top view of a fixture for assembling dental floss dispenser products showing the operation of loading a dispenser insert into a dispenser case in accordance with a preferred embodiment of the present invention.

Following the loading and threading of bobbin 410 in the insert threading station 330, conveyor assembly 300 carries the assembly fixture 200 to an insert loading station 340 where the insert 220 (with bobbin 410 loaded and threaded thereon) is driven into the dispenser case 240. Referring now to FIG. 6, there is shown a further top view of fixture assembly 200 illustrating the insert loading operation performed at loading station 340. In loading station 340, insert 220 is first detached from insert loading area 210 by exerting a downward force on latch release bar 252. While insert 220 is in its released state, a horizontal push bar 290 exerts a horizontal force against insert 220 in the direction shown by arrow 290a, thereby driving insert 220 into dispenser case 240. Following this operation, conveyor assembly 300 carries assembly fixture 200 first to lid closing station 250 where lid 244 of dispenser case 240 is placed in a closed position, and then to assembly removal station 360 where the completed dental floss product is removed from assembly fixture 200. As mentioned above, following station 360, the empty fixture assembly 200 is carried back to station 310 for re-use.

The present invention may be embodied in other specific forms without departing from the spirit or essential attributes of the invention. Accordingly, reference should be made to the appended claims, rather than the foregoing specification, as indicating the scope of the invention.

What is claimed is:

1. An apparatus for assembling a thread dispenser product formed of a bobbin of wound thread, a dispenser case, and a dispenser insert for rotatably supporting said bobbin of wound thread within said dispenser case, comprising:

(A) a singular assembly fixture having an insert loading area for holding said dispenser insert and a dispenser case loading area, separate from said insert loading area, for simultaneously holding said dispenser case, said insert loading area having a flat horizontal surface for mating with a bottom surface of said dispenser insert, said bottom surface of said dispenser insert having at least one opening;

(B) a moveable latching bar, pivotally coupled to said singular fixture assembly, for detachably securing said dispenser insert in said insert loading area, said moveable latching bar having a ridge for mating with said at least one opening in said bottom surface of said dispenser insert, said moveable latching bar being moveable between a locking position and a depressed position;

(C) second securing means, coupled to said singular assembly fixture, for detachably securing said dispenser case in said dispenser case loading area;

wherein said ridge in said moveable latching bar horizontally restrains said dispenser insert within said insert loading area when said moveable latching bar is in said locking position and said ridge is positioned within said at least one opening in said bottom of said dispenser insert, and said dispenser insert is free to move horizontally from said insert loading area toward said dispenser case loading area when said moveable latching bar is in said depressed position.

2. The apparatus of claim 1, wherein said bottom surface of said dispenser insert has first and second openings, and said moveable latching bar has first and second ridges for respectively mating with said first and second openings in said bottom surface of said dispenser insert.

3. The apparatus of claim 1, further comprising a spring for coupling said moveable latching bar to said singular assembly fixture.

4. The apparatus of claim 1, wherein said insert loading area and said dispenser case loading area are aligned along parallel horizontal planes.

5. The apparatus of claim 4, wherein said second securing means comprises a plurality of mounting pins and at least one spring loaded cam.

6. The apparatus of claim 5, said singular assembly fixture further comprising conveyor connection means for coupling said singular assembly fixture to a conveyor belt.

7. The apparatus of claim 6, wherein said wound thread is formed of a dental floss.

* * * * *